United States Patent [19]

Petroff et al.

[11] Patent Number: 5,059,704

[45] Date of Patent: Oct. 22, 1991

[54] FOLIAR-APPLIED HERBICIDAL COMPOSITIONS CONTAINING A SILICONE GLYCOL-SILICONE ALKANE TERPOLYMER ADJUVANT

[75] Inventors: Lenin J. Petroff, Bay County; David J. Romensko; Robert A. Ekeland, both of Midland County, all of Mich.

[73] Assignee: Dow Corning Corporation, Midland, Mich.

[21] Appl. No.: 581,360

[22] Filed: Sep. 12, 1990

Related U.S. Application Data

[60] Division of Ser. No. 450,342, Dec. 13, 1989, Pat. No. 4,990,175, and a continuation-in-part of Ser. No. 365,628, Jun. 13, 1989, abandoned.

[51] Int. Cl.$^5$ .............................................. C07F 7/08
[52] U.S. Cl. ................................... 556/437; 556/444; 556/445; 556/449; 556/450; 71/DIG. 1; 252/351; 252/352
[58] Field of Search ............... 556/445, 437, 444, 449, 556/450; 71/DIG. 1

[56] References Cited

U.S. PATENT DOCUMENTS

| | | | |
|---|---|---|---|
| 3,299,112 | 1/1967 | Bailey | 260/448.2 |
| 3,427,271 | 2/1969 | McKellar | 260/29.2 |
| 4,687,786 | 8/1987 | Kollmeier et al. | 521/110 |

FOREIGN PATENT DOCUMENTS 1255249 12/1971 United Kingdom ............... 556/437

OTHER PUBLICATIONS

Enhancement of Herbicides by Silicone Surfactants, L. L. Jansen, Mar. 1973, vol. 21, Issue 2, pp. 130–135.
Surface Active Copolymers, Union Carbide, Silicones, pp. 1–16.
Silwet ® Surfactants for Use in Agriculture.
Proceedings of the Thirty Eighth New Zealand Weed and Pest Control Conference, 1985.
Silicones for the Agricultural Industry, Union Carbide ® pp. 1–24.

*Primary Examiner*—Glennon H. Hollrah
*Assistant Examiner*—John D. Pak
*Attorney, Agent, or Firm*—Alexander Weitz

[57] ABSTRACT

There is disclosed a herbicidal composition in which a foliar-applied herbicide is activated by the inclusion of a silicone glycol-silicone alkane terpolymer adjuvant. The composition provides enhanced phytotoxicity in the control of narrowleaf weeds, particularly Barnyardgrass, Quackgrass and Johnsongrass, and often also shows an improved degree of rainfastness relative to similar herbicidal compositions employing prior art silicone glycol adjuvants.

3 Claims, No Drawings

FOLIAR-APPLIED HERBICIDAL COMPOSITIONS CONTAINING A SILICONE GLYCOL-SILICONE ALKANE TERPOLYMER ADJUVANT

This is a divisional of copending application Ser. No. 07/450,342 filed on 12/13/89 which is now U.S. Pat. No. 4,990,175, which is a continuation-in-part of Ser. No. 07/365,628, filed on June 13, 1989, now abandoned.

This invention relates to foliar-applied herbicide formulations. More particularly, the present invention relates to compositions of foliar-applied herbicides which are activated by the inclusion of certain silicone glycol-silicone alkane terpolymer adjuvants.

BACKGROUND OF THE INVENTION

It is well recognized in the art that the full efficacy of a given organic herbicide is not generally attained without the inclusion of various adjuvants, an adjuvant being broadly defined as any substance which enhances the effectiveness of the herbicide. Thus, for example, through proper formulation with an activity-increasing adjuvant, the control of a particular plant species by an herbicide can be greatly augmented. Such an activity-increasing adjuvant does not generally have biological activity on its own but only brings out the activity of the herbicide.

An example of the aforementioned activity-increasing adjuvants is the class of surfactants known as silicone glycols. These liquids have been shown to enhance the efficacy of various herbicides. L. L. Jansen (Weed Science, v. 21, pages 130–135, March, 1973) examined the effect of adding various silicone glycol adjuvants to different herbicides and reported that these adjuvants were superior to a standard organic surfactant in eight plant species. In this study, cationic amino silicone surfactants were also evaluated, but found to be less effective than the organic material. In any event, no specific structures of the silicone compounds were provided in this paper.

Great Britain Patent Number 1,255,249 to Dow Corning Corporation, published Dec. 1, 1971, again discloses herbicide compositions employing silicone glycol copolymers. Here, general utility of a large number of adjuvants is professed, as exemplified by two generic silicone glycol formulas which embrace structures having both diorganosiloxane units and alkyl-glycol siloxane units. There is also provided a wide-ranging list of suitable herbicides. This reference, however, provides little direction to those skilled in the art as to which particular silicone glycol structures are to be advantageously combined with specific herbicides, save for two examples employing a triazine herbicide in conjunction with an adjuvant having 1.8 siloxy units and bearing a glycol chain having 12 ethylene oxide units.

In addition to the herbicidal enhancement provided by the activity-increasing adjuvants discussed above, it is often important that herbicide formulations retain a significant degree of activity when plants treated therewith are exposed to rain shortly after application, this being a definition of the degree of "rainfastness." This is particularly critical for water-soluble foliar-applied herbicides, such as glyphosate salts, which may be washed away by rainfall occurring within about six hours of application. Typically, this problem is currently addressed by inclusion of another class of adjuvants in the herbicide formulation, namely sticking agents (see, for example, page 6 of *Adjuvants for Herbicides*, Weed Science Society of America, Champaign, Ill., 1982). The main function of these materials, as the appelation implies, is to impart an increased measure of adhesion of the herbicide composition to plant foliage and thus reduce premature washing away should precipitation occur after the plants are sprayed. The sticking agents are usually polymeric compounds which are generally water-soluble and tacky in nature.

Neither Jansen nor British Patent No. 1,255,249 addresses the issue of rainfastness nor does any reference suggest to those of ordinary skill in the art the use of applicants' particular silicone glycol-silicone alkane terpolymers to provide enhanced activity in conjunction with particular herbicides.

SUMMARY OF THE INVENTION

It has now been found that the efficacy of a foliar-applied herbicide can be synergistically increased by the inclusion of a silicone glycol-silicone alkane terpolymer in a herbicidally effective composition, "herbicidally effective" meaning that the composition provides the desired kill control of the particular weed in question. Moreover, this combination can provide increased rainfastness in the very same formulation without the need for an additional sticking agent.

The present invention therefore relates to a composition comprising:

(I) a foliar-applied herbicide; and
(II) from about 0.1 to about 10 parts by weight, for each part by weight of said herbicide (I), of a silicone glycol-silicone alkane terpolymer adjuvant having the average formula selected from the group consisting of

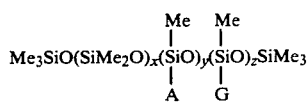

and

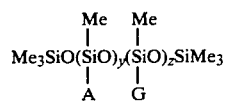

wherein Me denotes a methyl radical, A is a linear or branched alkyl radical having 6 to 24 carbon atoms, G is a glycol moiety having the formula $-R'(OCH_2CH_2)_mOZ$, in which $R'$ is a divalent alkylene group having 2 to 6 carbon atoms, Z is selected from the group consisting of hydrogen, an alkyl radical having 1 to 3 carbon atoms and an acyl group having 2 to 4 carbon atoms and m is 12 to 32, x is 0.01 to 3, y is 0.1 to 1.25 and z is 0.75 to 1.9, with the proviso that when the weight fraction of $-OCH_2CH_2-$ groups of said glycol moiety G is less than 0.7 said alkyl radical A contains from 6 to 12 carbon atoms and when the weight fraction of $-OCH_2CH_2-$ groups of said glycol moiety G is more than 0.8 said alkyl radical A contains from 8 to 24 carbon atoms.

The present invention further relates to a method for inhibiting the growth of narrowleaf annual and perennial weeds, particularly Barnyardgrass, Rhizone Johnsongrass and Rhizome Quackgrass, comprising contacting at least part of the weed with the aforementioned herbicidal composition.

DETAILED DESCRIPTION OF THE INVENTION

The herbicidal composition of the present invention is a homogeneous mixture comprising (I) a foliar-applied herbicide and (II) a silicone glycol-silicone alkane terpolymer adjuvant.

The foliar-applied herbicide (I) of the present invention is selected from those herbicides well known in the art to be effective when applied after the emergence of a plant.

Herbicides which are useful in this invention include triazines, ureas, carbamates, acetamides, uracils, acetic acid or phenol derivatives, triazoles, benzoic acids, nitriles, biphenyl ethers and the like such as:

Heterocyclic nitrogen/sulfur derivatives including 2-chloro-4-ethylamino-6-isopropylamino-s-triazine, 2-chloro-4,6-bis(isopropylamino-s-triazine; 2-chloro-4,6-bis(ethylamine)-s-triazine; 3-isopropyl-1H-2,1,3-benzothiadiazin-4-(3H)-one 2,2-dioxide, 3-amino-1,2,4-triazole; 5-bromo-3-isopropyl-6-methyluracil; 2-(4-isopropyl-4-methyl-5-oxo-2-imdazolin-2-yl-)3-quinolinecarboxylic acid; isopropylamine salt of 2-(4-methyl-5-oxo-2-imidazolin-2-yl)nicotinic acid, methyl 6-(4-isopropyl-4-methyl-5-oxo-2-imidazolin-2-yl)-m-toluate; and methyl 2-(4-isopropyl-4-methyl-5-oxo-2-imidazolin-2-yl)-p-toluate; and further including acids-/esters/alcohols such as (2,2-dichloropropionic acid; 2-methyl-4-chloropheno xyacetic acid, 2,4-dichlorophenoxyacetic acid, methyl-2-[4-(2,4-dichlorophenoxy)phenoxy]propionate, 3-amino-2,5-dichlorobenzoic acid, 2-methoxy-3,6-dichlorobenzoic acid, 2,3,6-trichlorophenylacetic acid, N-1-naphthylphthalamic acid, sodium 5-[2-chloro-4-(trifluoromethyl)phenoxy]-2-nitrobenzoate, 4,6-dinitro-o-sec-butylphenol, butyl 2-[-[(trifluoromethyl)-2-pyridinyl)oxy]-phenoxy]-propanoate; and cyclohexanediones such as sethoxydium and garlon and ethers such as 2,4-dichlorophenyl-4-nitrophenyl ether, 2-chloro-trifuluorop-tolyl-3-ethoxy-4-nitrodiphenyl ether, 5-(2-chloro-4-trifluoromethyl-phenoxy)-N-methylsulfonyl 2-nitrobenzamide, 1'-(carboethoxy) ethyl 5-[2-chloro-4-(trifluoromethyl)phenoxy]-2-nitrobenzoate and other diphenylethers and other miscellaneous herbicides such as 2,6-dichlorobenzonitrile, monosodium acid methanearsonate, disodium methanearsonate, 2-(2-chlorophenyl)methyl-4,4-dimethyl-3-isoxazolidinone.

One preferred foliar-applied herbicide is N-phosphonomethylglycine (glyphosate) or an agriculturally acceptable salt thereof. The isopropylamine salt of this compound is marketed under the trade name ROUNDUP (Monsanto Agricultural Products Co., St. Louis, Mo.), and is particularly preferred.

Other preferred herbicides of the present invention may be selected from sulfonylurea herbicides, such as those marketed by Du Pont (Wilmington, Del.) under the trade names ACCENT, HARMONY, CLASSIC, PINNACLE, EXPRESS, GLEAN, ALLY and FINESS. A particularly preferred herbicide of this class is 3-[4,6-bis(difluoromethoxy)-pyrimidin-2yl]-1-(2-methoxycarbonylphenylsulfonyl)-urea (common name: Primisulfuron). This material is marketed under the trade name BEACON (Ciba-Geigy Agricultural Division, Greensboro, N.C.).

The silicone glycol-silicone alkane terpolymer (II) of the present invention has the average structure selected from the group consisting of

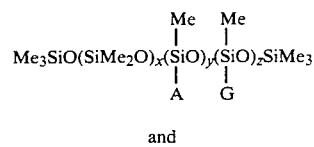

and

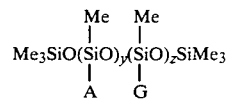

wherein Me hereinafter denotes a methyl radical, A is a linear or branched alkyl radical having 6 to 24 carbon atoms and G is a glycol moiety having the formula —R'(OCH$_2$CH$_2$)$_m$OZ, in which R' is a divalent alkylene group having 2 to 6 carbon atoms, Z is selected from the group consisting of hydrogen, an alkyl radical having 1 to 3 carbon atoms and an acyl group having 2 to 4 carbon atoms. In the above formulas, m is 12 to 32, x is 0.01 to 3, y is 0.1 to 1.25 and z is 0.75 to 1.9.

In addition to the above stated restrictions, it has been found that component (II) of the present invention must further be limited such that the number of carbon atoms of alkyl radical A is 6 to 12 when the calculated hydrophilic-lipophilic balance (HLB) of the terpolymer is less than 14 and the number of carbon atoms of A is 8 to 24 when the calculated HLB is greater than 16. The calculated HLB value is defined herein as the weight percent of ethylene oxide units (i.e., —OCH$_2$CH$_2$— units) in the terpolymer divided by 5. Thus, in order to be within the scope of the present invention, the number of carbon atoms of alkyl radical A is 6 to 12 when the weight fraction of ethylene oxide units is less than 0.7 and the number of carbon atoms of A is 8 to 24 when the weight fraction of ethylene oxide units is greater than 0.8.

A particularly preferred component (II) of the present invention has the average formula

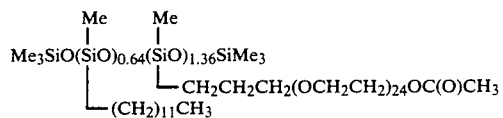

The silicone glycol-silicone alkane terpolymers described above may be prepared by methods well known in the art. Briefly, for example, the corresponding allyl-terminated glycol and alpha-alkene are coupled to an SiH-functional siloxane having the average structure

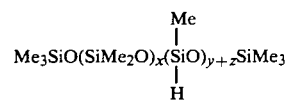

or

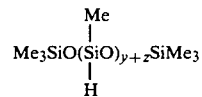

Coupling is accomplished in the presence of a platinum catalyst at temperatures in the range of about 20° C. to about 150° C., the reaction preferably being carried out at about 105° C. using an effective amount of a solvent such as toluene or isopropanol. The skilled artisan will recognize that, in such hydrosilylation reactions, a fraction of the allyl-terminated glycol and the alpha-alkene is not converted and will remain as an impurity in the final product terpolymer. The herbicidal compositions may contain such impurities and still be within the scope of the present invention.

In addition to the aforementioned components, the compositions of the present invention may also contain other herbicide adjuvants commonly employed in the art.

The phytotoxicant compositions of this invention, preferably contain (in addition to the herbicide active and silicone) an inert adjuvant or conditioning agent and one or more surface-active agents in amounts sufficient to render a given composition readily dispersible in water or in oil. The incorporation of a surface active agent into the compositions of this invention greatly enhances their efficacy. By the term surface active agent, it is understood that wetting agents, dispersing agents, suspending agents and emulsifying agents are included therein. Anionic, cationic and nonionic agents can be employed with equal facility.

Preferred wetting agents are alkyl benezene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkyl phenols (particularly isooctylphenol and nonylphenol), polyoxyethylene derivatives of fatty acid esters of hexito anyhydrides (sorbitan) and silicone glycols. Preferred dispersants are methylcellulose, polyvinylalcohol, sodium lignin sulfonates, polymeric alkyl naphthalene sulfonates, sodium naphthalene sulfonate, polymethylene bisnaphthalenesulfonates and sodium N-methyl-N-long chain acid laurates.

Suitable surfactants (adjuvants) are disclosed in U.S. Pat. Nos. 3,799,758 and 4,405,531, both of which are incorporated herein in their entirety by reference. Examples of other adjuvants include crop oil concentrate, ORTHO X-77 spreader, drift control agents, such as LO-DRIFT, defoaming agents, such as D-FOAMER, compatibility agents, such as E-Z MIX, and other adjuvants well known in the herbicide art.

In order to prepare the compositions of the present invention, from about 0.1 to about 10 parts by weight of the silicone glycol-silicone alkane terpolymer (II) is thoroughly mixed with each part by weight of herbicide (I). Preferably, from 0.5 to 4 parts by weight of (II) are employed for each part of the pesticide (I). For a given herbicide, the skilled artisan will readily arrive at a herbicidal composition having the optimum ratio of the ingredients by routine experimentation.

The above herbicidal composition may then be dispersed in water and sprayed onto plants according to the method of the present invention, described infra. Alternatively, the silicone glycol-silicone alkane terpolymer adjuvant (II) may be added directly to a water solution or dispersion of herbicide (I).

The present invention also relates to a method for inhibiting the growth of narrow-leaf weeds, particularly the species *Echinochloa crus-galli*, hereinafter referred to by its common name of "Barnyardgrass," *Agropyron repens*, hereinafter referred to by its common name of "Quackgrass" and *Sorghum halepense*, hereinafter referred to by its common name "Johnsongrass." This method comprises contacting at least part of the weed with the above described herbicidal composition. This composition, usually in water dispersion form, is applied to the foliage of the weed by any of the methods commonly practiced in the art, preferably by spraying. The composition may be either a package mix or a tank mix. The amount of the dispersion, and the herbicide contained therein, to be applied to the weed may be varied to a great extent, the optima being determined by such factors as soil conditions, weather conditions and the type of crops or other plants growing alongside the weed. Generally, however, the effective application rate is about 0.5 to 10 pounds per acre of herbicide formulation. The skilled artisan is directed to U.S. Pat. Nos. 3,799,758 and 4,405,531, hereby incorporated by reference, for further suggestions as to appropriate application rates for N-phosphonomethylglycine based herbicides.

When the compositions of the present invention are used according to the above described method, there is observed a statistically significant improvement in the efficacy and/or rainfastness of the herbicidal compositions relative to compositions employing prior art silicone glycol adjuvants or only the unmodified herbicide. There is provided a distinct advantage by the instant compositions in that they permit the use of lower herbicide levels to attain a similar degree of injury to a weed, this advantage often being maximized when there is a reasonable likelihood of precipitation after applying the herbicide. Such a reduction in herbicide levels generally results in reduced injury to adjacent cash crops and is considered highly desirable.

EXAMPLES

The following examples are presented to further illustrate the compositions of this invention, but are not to be construed as limiting the invention, which is delineated in the appended claims. All parts and percentages in the examples are on a weight basis unless indicated to the contrary.

EXAMPLES 1-10

A silicone glycol-silicone alkane terpolymer adjuvant of the present invention was prepared as follows. A three neck 1 liter flask, equipped with nitrogen inlet/thermometer, claisen head with addition funnel/condenser and mechanical air driven stirrer was charged with 50.37 g (0.17 mole) of an SiH-functional siloxane having the average formula

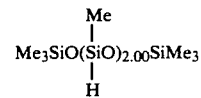

24.2 g (0.14 mole) of alpha-dodecene, 398.2 g (0.32 mole) of an allyl-functional glycol having the formula $CH_2=CHCH_2(OCH_2CH_2)_{24}OC(O)CH_3$ and 0.2 g of sodium acetate. Dissolved air was removed from the mixture under vacuum, the flask was purged with nitrogen gas and the contents heated to 140° C. The stirred mixture was then catalyzed with 10 ppm of chloroplatinic acid (as a 1% solution in isopropyl alcohol). The exothermic reaction brought the temperature of the mixture to 155° C. The mixture was held at a temperature of 150° C. for 2 hours, after which all of the initial SiH functionality had reacted, as determined by IR analysis. The mixture was cooled to 50° C. and 0.5 wt % Nucap 200, 0.5 wt % Celite 545 (filtration aids) and 150 g of isopropanol were added. This mixture was stirred for one hour, pressure filtered and the isopropanol solvent vacuum stripped off to provide 423.5 g (90% yield) of a final product having the calculated average formula

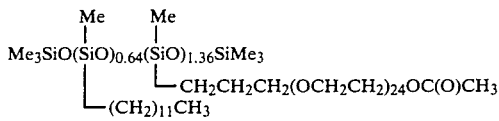

wherein Me hereinafter denotes a methyl radical. This product is designated as FLUID A in Table 1.

A similar procedure was employed to prepare other silicone glycol-silicone alkane terpolymers (FLUIDS B-G) and comparative silicone glycols (FLUIDS J-K), also shown in Table 1. These fluids had the average formula

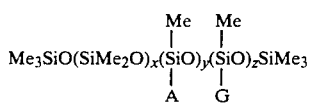

wherein A is a normal alkyl radical having n carbon atoms, G is an acetoxy terminated glycol moiety having the formula $-CH_2CH_2CH_2(OCH_2CH_2)_mOC(O)CH_3$, the values of m, n, x, y and z for the various terpolymers being given in Table 1, below.

TABLE 1

| FLUID | n | m | x | y | z |
|---|---|---|---|---|---|
| A | 12 | 24 | 0 | 0.64 | 1.36 |
| B | 12 | 24 | 8.5 | 1.00 | 4.50 |
| C | 12 | 24 | 2.00 | 1.50 | 2.50 |
| D | 12 | 4 | 8.50 | 0.50 | 5.00 |
| E | 12 | 4 | 2.00 | 0.50 | 3.50 |
| F | 12 | 4 | 0 | 0.25 | 1.75 |
| G | 12 | 12 | 19.00 | 2.00 | 9.00 |
| H | 12 | 12 | 0 | 0.64 | 1.36 |
| I | 8 | 12 | 0 | 0.73 | 1.27 |
| J | — | 7 | 0 | 0 | 1.00 |
| K* | — | 4 | 0 | 0 | 1.00 |
| L-77** | | | | | |

*glycol terminated with $-OH$ instead of $-OC{=}O$
$\qquad\qquad\qquad\qquad\qquad\qquad\qquad\quad |$
$\qquad\qquad\qquad\qquad\qquad\qquad\qquad CH_3$
**SILWET L-77 (Union Carbide Corp., Danbury, CT)

Comparative silicone glycol adjuvants used in the following evaluations of herbicidal activity included:
FLUID J, described in Table 1.
FLUID K, also described in Table 1.
SILWET L-77 (Union Carbide Corp., Danbury, Conn.) is described as a silicone glycol surfactant for use in agriculture.

TEST PROTOCOL

The following weed species were used as indicator weeds:

| Common Name | Scientific Name |
|---|---|
| Rhizome Quakgrass | Agropyron repens |
| Rhizome Johnsongrass | Sorghum halepense |
| Barnyardgrass | Echinochloa crus-galli |
| Velvetleaf (a broadleaf) | Abutilon theophrasti |

The narrowleaf and broadleaf test weeds were seeded separately into plastic pots 4 inches in diameter and 3 inches deep with drainage holes on the bottom. The pots contained Dupo silt loam soil obtained from the St. Charles Research Farm of Monsanto Company located in St. Charles, Mo. Prior to use, the soil was steam sterilized at a temperature of 180° F. The soil used was mixed with a slow release 14-14-14 fertilizer.

Barnyard grass and velvetleaf were started from seeds while rhizome johnsongrass and rhizome quackgrass plants were grown from rhizome pieces. In all cases, sufficient seeds or stock propagules were planted to produce several seedlings in each pot. Approximately 7 to 10 days after seeding, the velvetleaf seedlings were thinned out leaving 2 to 3 healthy seedlings per pot.

After the pots were seeded, the pots were moved into the greenhouse, or a growth chamber, and placed on trays with each tray holding 40 to 60 pots. The trays were lined with absorbent mats for subirrigation. The greenhouse temperature was maintained at 86° F. during the day and 70° F. during the night while the growth chamber was maintained at 15° C. day temperature and 9° C. night temperature. Photoperiod in the greenhouse was maintained at 14 to 16 hours daylength using supplemental lighting, and 10 hours in the growth chamber. The seeded pots were watered via subirrigation as required.

Depending on the weed species used in a given test, the chemical treatments were applied within 14 to 60 days after planting. At that time, the narrowleaf weeds were approximately 4 to 16 inches tall while the broadleaf weeds were 1 to 4 inches tall.

Chemical treatments were applied post-emergence with the foliage of the weeds as the locus of application using a tract sprayer equipped with a single 8001E spray nozzle. The sprayer was previously calibrated to deliver a spray volume equivalent to about 20 gallons per acre of spray solution at a spraying pressure of about 30 psi.

The chemical compositions illustrative of compositions of this invention used in the tests were formulated as tank mixtures the same day of application. The formulations comprised Roundup ® (an agriculturally acceptable salt of N-phosphonomethylglycine, namely the isopropylamine salt, and inert adjuvant as a surfactant) a silicone copolymer and water.

Rates of application based on N-phosphonomethyglycine ranged from about ⅛ to about 3 pounds glyphosate acid equivalent per acre. The ingredient ratios employed in the formulations were glyphosate to silicone of about 1:0.1 to 1:10. Rainfall treatment was applied one hour after spraying of the compositions using a rain tower calibrated to deliver approximately ¼ inch of simulated rainfall within a period of about 15 minutes.

After application of rainfall, the treated plants were placed on carts and moved into the greenhouse. After the plants had sufficiently dried out, the pots were returned to the greenhouse (growth chamber) trays and arranged in a randomized complete block experimental design. Each treatment contained 3 replications. Control plants and appropriate standard treatments were provided in each test. A duplicate set of plants which received the same treatment and which were treated in a similar manner as the rainfall treated plants were also provided for comparison under no rain condition.

Observations on the effects of the treatments were taken within 7 to 10 days for early burndown effects and again within 21 to 28 days after treatment for longer term effects. A rating scale of 0% to 100% was used in estimating the degree of weed control with 0% having no observable effect and 100% as complete kill of the weed. The degree of burn, chlorosis, necrosis, stature reduction, and other observable effects of the treatments on plant species present in the test were taken into consideration in making the ratings. Ten examples follow which illustrate compositions and method of use of this invention.

EXAMPLE 1

Response to barnyardgrass (BYGR) and velvetleaf (VELE) to tank mixtures containing Roundup ® and silicones with or without ¼ inch of simulated rainfall—final rating.

| Treatment | Rain (inches) | Average % Inhibition (25 DAT)* | |
|---|---|---|---|
| | | BYGR | VELE |
| Roundup ® + 0.25% FLUID A | 0 | 100 a | 100 a |
| | ¼ | 30 d-g | 37 def |
| Roundup ® + 1% FLUID A | 0 | 100 a | 100 a |
| | ¼ | 87 a | 60 bcd |
| Roundup ® | 0 | 100 a | 100 a |
| | ¼ | 28 d-h | 73 abc |
| Roundup ® + 0.25% L-77 | 0 | 63 bc | 100 a |
| | ¼ | 10 f-i | 100 a |
| Roundup ® + 1% L-77 | 0 | 77 ab | 100 a |
| | ¼ | 5 hi | 100 a |
| Roundup ® + 0.25% FLUID J | 0 | 50 cd | 100 a |
| | ¼ | 12 e-i | 100 a |
| Roundup ® + 1% FLUID J | 0 | 20 e-i | 100 a |
| | ¼ | 7 ghi | 100 a |
| Roundup ® + 0.25% FLUID H | 0 | 100 a | 100 a |
| | ¼ | 23 e-i | 20 fgh |
| Roundup ® + 1% FLUID H | 0 | 100 a | 99 a |
| | ¼ | 33 def | 17 fgh |
| Roundup ® + 0.25% FLUID I | 0 | 97 a | 100 a |
| | ¼ | 20 e-i | 3 gh |
| Roundup ® + 1% FLUID I | 0 | 100 a | 100 a |
| | ¼ | 10 f-i | 33 d-g |
| Roundup ® + 0.25% FLUID B | 0 | 100 a | 99 a |
| | ¼ | 35 de | 53 cde |
| Roundup ® + 1% FLUID B | 0 | 100 a | 100 a |
| | ¼ | 15 e-i | 28 e-h |
| Untreated Control | — | 0 i | 0 h |

Notes:
Roundup ® was applied at ⅜ lb ae/A (ae = acid equivalent of glyphosate).
Additive concentrations shown are based on percent of total spray volume.
All treatments were applied at a spray gallonage equivalent to 20 gallons/A of spray solution.
L77 = Silwet L-77, Union Carbide silicone Surfactant.
Rainfall treatment equivalent to ¼ inch of rain was applied approximately one hour after herbicidal treatment for a period of 15 minutes.
Values shown are averages of three replications per treatment.
Means followed by different letters within weed species are significantly different from one another at the 0.05 probability level using Duncan's Multiple Range Test.
*DAT = Days after treatment

EXAMPLE 2

Effects of silicones as Roundup ® additives on rhizome quackgrass.

| Treatment | Glyphosate Rate (⅜ lb ae/A) Average % Inhibition (28 dat) QUACKGRASS | |
|---|---|---|
| | 0 Rain | 0.25" Rain |
| Roundup ® + 0.25% FLUID A | 96 ab | 60 fgh |
| Roundup ® + 1% FLUID A | 100 a | 82 a-e |
| Roundup ® | 95 ab | 40 i |
| Roundup ® + 0.25% L-77 | 81 a-e | 50 hi |
| Roundup ® + 1% L-77 | 85 a-e | 70 d-g |
| Roundup ® + 0.25% FLUID J | 99 ab | 55 ghi |
| Roundup ® + 1% FLUID J | 83 a-e | 75 c-f |
| Roundup ® + 0.25% FLUID C | 91 abc | 58 f-i |
| Roundup ® + 1% FLUID C | 100 a | 66 e-h |
| Roundup ® + 0.25% FLUID G | 98 ab | 79 b-e |
| Roundup ® + 1% FLUID G | 98 ab | 71 d-g |
| Roundup ® + 0.25% FLUID B | 100 a | 57 f-i |
| Roundup ® + 1% FLUID B | 99 ab | 60 fgh |

Values shown are averages of three replications per treatment.

EXAMPLE 3

Response of barnyardgrass to tank mixtures containing Roundup ® and silicone in the absence or presence of ¼ inch simulated rainfall applied one hour after treatment. Data show average percent growth inhibition 25 days after treatment. Roundup ® was applied at ⅜ lb ae/A; silicones at 0.25% (v/v). The spray gallonage was equivalent to 20 gallons per acre of spray solution.

| Treatment | Average % Inhibition (25 DAT) | |
|---|---|---|
| | 0 Rain | 0.25" Rain |
| Roundup ® + FLUID A | 100 a | 30 de |
| Roundup ® | 95 a | 12 fgh |
| Roundup ® + FLUID D | 20 ef | 0 h |
| Roundup ® + FLUID E | 40 d | 0 oh |
| Roundup ® + FLUID F | 40 d | 2 gh |
| Roundup ® + FLUID C | 100 a | 3 gh |

-continued

| Treatment | Average % Inhibition (25 DAT) | |
|---|---|---|
| | 0 Rain | 0.25" Rain |
| Roundup ® + FLUID B | 100 a | 5 fgh |

EXAMPLE 4

Response of barnyardgrass to tank mixtures containing Roundup ® and silicone in the absence or presence of ¼ inch simulated rainfall applied one hour after treatment. Data show average percent growth inhibition 24 days after treatment.

| Treatment | Rain (inches) | Average % Inhibition (24 DAT) | |
|---|---|---|---|
| | | ⅜ lb ae/A | ½ lb ae/A |
| Roundup ® + 1% FLUID A | 0 | 100 a | 100 a |
| | ¼ | 27 g–m | 63 b–f |
| Roundup ® | 0 | 100 a | 100 a |
| | ¼ | 18 i–m | 23 g–m |
| Roundup ® + 1% FLUID J | 0 | 20 h–m | 33 f–l |
| | ¼ | 23 g–m | 50 c–h |

Note:
Silicone concentrations are expressed as % of total spray volume based on a spray gallonage equivalent to 20 gallons/A.
Means followed by differenc letters are significantly different from one another at the 5% probability level based on Duncan's Multiple Range Test.

EXAMPLE 5

Response of rhizome johnsongrass to tank mixtures containing Roundup ® and silicone in the absence or presence of ¼ inch simulated rainfall applied one hour after treatment. Data show average percent growth inhibition 23 days after treatment.

| Treatment | Rain (inches) | Average % Inhibition (23 DAT) | |
|---|---|---|---|
| | | ⅜ lb ae/A | ½ lb ae/A |
| Roundup ® + 1% FLUID A | 0 | 99 a | 100 a |
| | ¼ | 76 ab | 87 ab |
| Roundup ® | 0 | 53 cd | 8 c |
| | ¼ | 91 ab | 40 d |
| Roundup ® + 1% L-77 | 0 | 89 ab | 99 a |
| | ¼ | 99 a | 100 a |
| Roundup ® + 1% FLUID J | 0 | 100 a | 100 a |
| | ¼ | 100 a | 100 a |

Note:
Silicone concentrations are expressed as % of the total spray volume based on a spray gallonage equivalent to 20 gallons/A.
Means followed by different letters are significantly different from one another at the 5% probability level based on Duncan's Multiple Range Test.

EXAMPLE 6

Response of rhizome johnsongrass to tank mixtures containing Roundup ® and silicone in the absence or presence of ¼ inch simulated rainfall applied one hour after treatment. Data show average percent growth inhibition 28 days after treatment. Roundup ® was applied at ⅜ lb ae/A. The spray gallonage was equivalent to 20 gallons per acre of spray solution.

| Silicone Additive | Silicone Conc. (%) | Average % Inhibition (28 DAT) | |
|---|---|---|---|
| | | 0 Rain | 0.25" Rain |
| FLUID A | 0.0625 | 93 a | 0 e |
| | 0.125 | 84 ab | 0 e |
| | 0.25 | 82 ab | 3 e |
| | 0.5 | 93 a | 2 e |
| | 1 | 98 a | 0 e |
| NONE | — | 15 e | 0 e |
| FLUID J | 0.0625 | 3 e | 0 e |
| | 0.125 | 13 e | 0 e |
| | 0.25 | 45 d | 5 e |
| | 0.5 | 96 a | 53 cd |
| | 1 | 92 a | 70 bc |
| FLUID K | 0.0625 | 3 e | 0 e |
| | 0.125 | 0 e | 0 e |
| | 0.25 | 10 e | 0 e |
| | 0.5 | 2 e | 2 e |
| | 1 | 2 e | 2 e |
| FLUID E | 0.0625 | 13 e | 0 e |
| | 0.125 | 12 e | 0 e |
| | 0.25 | 0 e | 0 e |
| | 0.5 | 13 e | 0 e |
| | 1 | 5 e | 3 e |

Note:
Silicone concentrations are expressed as % of the total spray volume based on a spray gallonage equivalent to 20 gallons/A.

EXAMPLE 7

Response of rhizome johnsongrass to tank mixtures containing Roundup ® and silicone in the absence or presence of ¼ inch simulated rainfall applied one hour after treatment. Roundup ® was applied at ½ lb ae/A and silicones at 0.5% (v/v). The spray gallonage was equivalent to 20 gallons per acre of spray solution.

| Silicone Additive | Average % Inhibition (22 DAT) | |
|---|---|---|
| | 0 Rain | 0.25" Rain |
| FLUID A | 90 a–d | 73 a–g |
| NONE | 95 ab | 27 ijk |
| FLUID J | 52 f–i | 68 c–h |
| FLUID E | 13 kl | 5 kl |
| FLUID F | 18 kl | 7 kl |
| FLUID B | 92 a–d | 60 e–h |

EXAMPLE 8

Effect of Roundup ® rate and silicone content on rhizome quackgrass without rain and 28 days after treatment. Roundup ® rates of ¼ and ⅜ lb ae/A were based on N-phosphonomethylglycine content.

| | Average % Inhibition (28 DAT) | |
|---|---|---|
| | ¼ lb ae/A | ⅜ lb ae/A |
| Roundup ® + 0.0625% FLUID A | 77 e–h | 88 a–e |
| Roundup ® + 0.125% FLUID A | 93 ab | 91 abc |
| Roundup ® + 0.25% FLUID A | 89 a–e | 91 abc |
| Roundup ® + 0.50% FLUID A | 88 a–e | 89 a–e |
| Roundup ® + 1% FLUID A | 90 a–d | 91 abc |
| Roundup ® | 71 gh | 83 a–f |
| Roundup ® + 0.0625% FLUID B | 79 d–h | 89 a–d |
| Roundup ® + 0.125% FLUID B | 88 a–e | 87 a–e |
| Roundup ® + 0.25% FLUID B | 85 a–f | 95 a |
| Roundup ® + 0.50% FLUID B | 92 abc | 89 a–e |
| Roundup ® + 1% FLUID B | 93 ab | 85 a–f |
| Roundup ® + 0.0625% FLUID C | 69 h | 84 a–f |
| Roundup ® + 0.125% FLUID C | 77 e–h | 92 abc |
| Roundup ® + 0.25% FLUID C | 82 b–g | 91 abc |
| Roundup ® + 0.50% FLUID C | 85 a–f | 89 a–d |
| Roundup ® + 1% FLUID C | 82 b–g | 87 a–e |
| Roundup ® + 0.0625% FLUID J | 58 i | 81 c–g |
| Roundup ® + 0.125% FLUID J | 49 ij | 82 b–g |
| Roundup ® + 0.25% FLUID J | 41 j | 75 fgh |
| Roundup ® + 0.50% FLUID J | 47 j | 58 i |

-continued

| | Average % Inhibition (28 DAT) | |
|---|---|---|
| | ¼ lb ae/A | ⅜ lb ae/A |
| Roundup ® + 1% FLUID J | 68 h | 75 fgh |

EXAMPLE 9

Response of rhizome quackgrass to tank mixtures containing Roundup ® and silicone in the absence or presence of ¼ inch simulated rainfall applied one hour after treatment. Data show average percent growth inhibition 28 days after treatment. Roundup ® was applied at ½ lb ae/A.

| | Average % Inhibition (28 DAT) | |
|---|---|---|
| Treatment | 0 Rain | 0.25" Rain |
| Roundup ® + 0.10% FLUID A | 100 a | 95 abc |
| Roundup ® + 0.25% FLUID A | 98 ab | 87 cd |
| Roundup ® + 1.00% FLUID A | 99 ab | 94 abc |
| Roundup ® | 99 ab | 70 e |
| Roundup ® + 0.10% L-77 | 100 a | 91 abc |
| Roundup ® + 0.25% L-77 | 98 ab | 96 abc |
| Roundup ® + 1.00% L-77 | 100 a | 96 abc |
| Roundup ® + 0.10% FLUID I | 99 ab | 79 d |
| Roundup ® + 0.25% FLUID I | 99 ab | 93 abc |
| Roundup ® + 1.00% FLUID I | 99 ab | 88 bc |

Note:
Silicone concentrations are expressed as % of the total spray volume based on a spray gallonage equivalent to 20 gallons/A.
Means followed by different letters are significantly different from one another at the 5% probability level based on Duncan's Multiple Range Test.

EXAMPLE 10

Response of rhizome quackgrass to tank mixtures containing Roundup ® and silicone without rainfall treatment. Data show average percent growth inhibition 28 days after treatment.

| | Average % Inhibition (28 DAT) | |
|---|---|---|
| Treatment | ¼ lb ae/A | ⅜ lb ae/A |
| Roundup ® + 0.0625% FLUID A | 75 c-j | 80 a-f |
| Roundup ® + 0.125% FLUID A | 75 c-j | 95 a |
| Roundup ® + 0.25% FLUID A | 74 d-j | 89 a-d |
| Roundup ® + 0.5% FLUID A | 79 a-g | 95 a |
| Roundup ® + 1% FLUID A | 89 a-d | 93 ab |
| Roundup ® | 59 hij | 73 d-j |
| Roundup ® + 0.0625% FLUID B | 78 a-h | 71 e-k |
| Roundup ® + 0.125% FLUID B | 68 e-k | 92 abc |
| Roundup ® + 0.25% FLUID B | 83 a-e | 90 a-d |
| Roundup ® + 0.5% FLUID B | 78 a-h | 89 a-d |
| Roundup ® + 1% FLUID B | 82 a-e | 89 a-d |
| Roundup ® + 0.0625% FLUID C | 59 hij | 75 c-j |
| Roundup ® + 0.125% FLUID C | 75 c-j | 76 b-i |
| Roundup ® + 0.25% FLUID C | 88 a-d | 80 a-f |
| Roundup ® + 0.5% FLUID C | 79 a-g | 78 a-h |
| Roundup ® + 1% FLUID C | 74 d-j | 83 a-e |
| Roundup ® + 0.0625% FLUID J | 68 e-k | 73 d-j |
| Roundup ® + 0.125% FLUID J | 62 g-k | 73 d-j |
| Roundup ® + 0.25% FLUID J | 54 k | 61 h-k |
| Roundup ® + 0.5% FLUID J | 58 jk | 67 e-k |
| Roundup ® + 1% FLUID J | 68 e-k | 73 d-j |
| Roundup ® + 0.125% Roundup surfactant | 64 f-k | 75 c-j |
| Roundup ® + 0.5% Roundup surfactant | 73 d-j | 80 a-f |

-continued

| | Average % Inhibition (28 DAT) | |
|---|---|---|
| Treatment | ¼ lb ae/A | ⅜ lb ae/A |

Note:
Additive concentrations are expressed as % of the total spray volume based on a spray gallonage equivalent to 20 gallons/A.
Means followed by different letters are significantly different from one another at the 5% probability level based on Duncan's Multiple Range Test.

EXAMPLES 11-42

The adjuvant terpolymers shown in Table 2, and having the average structure

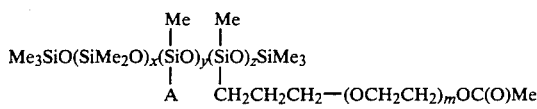

wherein A is a normal alkyl radical having 6 to 24 carbon atoms, were prepared according to the above described methods. These terpolymer adjuvants were mixed at a 0.5% level with BEACON herbicide (Ciba-Geigy Agricultural Division) and applied to plants as described infra.

TEST PROTOCOL

Individually potted Johnsongrass plants were grown from seeds under standard greenhouse conditions in BACCTO professional potting soil mix. Temperature was controlled at $75° +/- 2°$ F. Irradiation consisted of normal sunlight supplemented by high-pressure sodium vapor lamps to provide an added 1,200 $\mu E/m^2 \cdot s$ at bench level ($\mu E$ = microeinstein), wherein the day/night cycle was set at 18 hours and 6 hours, respectively.

Fourteen days after planting, when the plants were at the three-leaf stage, they were sprayed with water dispersions of the herbicide compositions so as to broadcast herbicide (i.e., BEACON) at a rate of 0.5 grams (active ingredient) per acre (0.5 g ai/A) along with the adjuvant (i.e., above described terpolymer) at a rate of 1 pint/A. Spraying was accomplished by means of a link-belt sprayer fitted with a TEEJET 8001 E nozzle which delivered the equivalent of 25 gallons/acre of the herbicide dispersion. The BEACON application rate employed was previously found to induce approximately 50% injury to the Johnsongrass after 14 days when a commercial adjuvant, ORTHO X-77 spreader (Chevron Chemical Co., San Francisco, Calif.), was mixed with the BEACON and broadcast at the above rates.

In addition, the rainfastness of the herbicide compositions was evaluated by spraying half the plants with water in order to simulate rainfall. This procedure consisted of spraying plants from above (8-10 inches above plant tops) using a TEEJET nozzle which delivered 0.4 gallons of water per minute. This nozzle was also mounted on a chain drive and reciprocally moved over four plants at a time, each such traverse taking about 9-10 seconds. The water spray was started 30 minutes after application of the herbicide compositions and was continued for approximately 7 minutes, at which point the equivalent of one inch of "rain" had fallen on each plant.

Plant injury was visually determined using a double-blind experimental mode wherein four replicates were run for each herbicide composition. Phytotoxicity was ranked from zero, corresponding to no observable effect, to 100%, corresponding to total destruction of the plant. These results were averaged and the values reported using the above mentioned Duncan's multiple range test to distinguish statistical differences at the 95% confidence level.

The above described herbicide dispersions were used to spray plants and the degree of injury, both with and without rain simulation, was observed 14 days after spraying with the herbicide dispersions. These results, along with the Duncan statistical annotations, are presented in Table 2. For additional comparison, results from spraying with BEACON+ORTHO X-77, BEACON alone (i.e., without adjuvant) and from controls which were not sprayed with herbicide, are also reported in Table 2.

$)_m OZ$, in which R' is a divalent alkylene group having 2 to 6 carbon atoms, Z is selected from the group consisting of hydrogen, an alkyl radical having 1 to 3 carbon atoms and an acyl group having 2 to 4 carbon atoms and m is 12 to 32, y is 0.1 to 1.25 and z is 0.75 to 1.9, with the proviso that when the weight fraction of $-OCH_2CH_2-$ groups of said terpolymer is less than 0.7 said alkyl radical A contains from 6 to 12 carbon atoms and when the weight fraction of $-OCH_2CH_2-$ groups of said terpolymer is more than 0.8 said alkyl radical A contains from 8 to 24 carbon atoms.

2. The terpolymer according to claim 1 wherein said terpolymer has the average structure

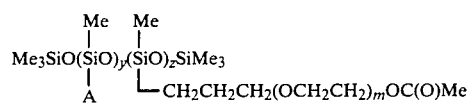

TABLE 2

| | Silicone-Glycol-Silicone Alkane Terpolymer | | | | | | Percent Injury to Plant | |
|---|---|---|---|---|---|---|---|---|
| | | | No. of carbons in | | | | | |
| | x | y | Alkyl Radical A | z | m | HLB | No Rain | With Rain |
| Example | | | | | | | | |
| 11 | 0 | 0.10 | 24 | 1.90 | 12 | 14.41 | 99$^a$ | 45$^c$ |
| 12 | 0 | 0.10 | 12 | 1.90 | 12 | 14.57 | 96$^a$ | 23$^{d-i}$ |
| 13 | 0 | 1.14 | 8 | 0.86 | 24 | 13.49 | 96$^a$ | 23$^{d-i}$ |
| 14 | 0 | 0.40 | 12 | 1.60 | 12 | 13.52 | 95$^a$ | 33$^{cde}$ |
| 15 | 0 | 1.00 | 8 | 1.00 | 32 | 15.28 | 94$^a$ | 13$^{g-j}$ |
| 16 | 0 | 0.10 | 8 | 1.90 | 12 | 14.62 | 94$^a$ | 25$^{d-h}$ |
| 17 | 0 | 1.25 | 12 | 0.75 | 32 | 13.43 | 94$^a$ | 13$^{g-j}$ |
| 18 | 0 | 0.53 | 12 | 1.47 | 32 | 16.50 | 91$^a$ | 13$^{g-j}$ |
| 19 | 0 | 0.10 | 12 | 1.90 | 24 | 16.75 | 90$^a$ | 13$^{g-j}$ |
| 20 | 0 | 0.14 | 24 | 1.86 | 24 | 16.51 | 90$^a$ | 10$^{hij}$ |
| 21 | 0 | 0.64 | 12 | 1.35 | 24 | 15.24 | 90$^a$ | 15$^{f-j}$ |
| 22 | 0 | 0.64 | 12 | 1.36 | 24 | 15.25 | 89$^a$ | 15$^{f-j}$ |
| 23 | 0 | 0.14 | 24 | 1.86 | 24 | 16.51 | 88$^a$ | 15$^{f-j}$ |
| 24 | 0 | 0.65 | 12 | 1.35 | 24 | 15.22 | 88$^a$ | 10$^{hij}$ |
| 25 | 0 | 0.51 | 6 | 1.49 | 12 | 13.51 | 88$^a$ | 18$^{e-i}$ |
| 26 | 0 | 1.20 | 6 | 0.80 | 24 | 13.43 | 88$^a$ | 10$^{hij}$ |
| 27 | 0 | 0.53 | 12 | 1.47 | 32 | 16.50 | 86$^a$ | 10$^{hij}$ |
| 28 | 0 | 0.70 | 24 | 1.30 | 32 | 15.24 | 85$^a$ | 15$^{f-j}$ |
| 29 | 0 | 1.14 | 8 | 0.86 | 24 | 13.49 | 85$^a$ | 23$^{d-i}$ |
| 30 | 0 | 0.25 | 8 | 1.75 | 24 | 16.50 | 84$^a$ | 23$^{d-i}$ |
| 31 | 0 | 0.30 | 6 | 1.70 | 24 | 16.45 | 70$^b$ | 15$^{f-j}$ |
| 32 | 0 | 1.05 | 6 | 0.95 | 32 | 15.28 | 70$^b$ | 10$^{hij}$ |
| 33 | 0 | 0.10 | 6 | 1.90 | 12 | 14.65 | 70$^b$ | 38$^{cd}$ |
| Comparative Examples | | | | | | | | |
| 34 | 2 | 1.50 | 12 | 2.50 | 24 | 14.89 | 38$^{cd}$ | 15$^{f-j}$ |
| 35 | 0 | 1.55 | 8 | 0.45 | 50 | 13.56 | 38$^{cd}$ | 25$^{d-h}$ |
| 36 | 0 | 1.65 | 8 | 0.35 | 100 | 15.25 | 35$^{cd}$ | 25$^{d-h}$ |
| 37 | 0 | 0.82 | 24 | 1.18 | 24 | 13.52 | 30$^{def}$ | 28$^{d-g}$ |
| 38 | 0 | 1.40 | 24 | 0.60 | 100 | 15.45 | 28$^{d-g}$ | 28$^{d-g}$ |
| 39 | 0 | 0.65 | 6 | 1.35 | 32 | 16.51 | 25$^{d-h}$ | 18$^{e-i}$ |
| 40 | 0 | 1.40 | 12 | 0.60 | 97 | 16.50 | 25$^{d-h}$ | 15$^{f-j}$ |
| 41 | 0 | 1.30 | 24 | 0.70 | 50 | 13.50 | 25$^{d-h}$ | 23$^{d-i}$ |
| 42 | 0 | 1.70 | 12 | 0.30 | 100 | 13.92 | 18$^{e-i}$ | 15$^{f-j}$ |
| BEACON + ORTHO X-77 | | | | | | | 63$^b$ | 13$^{g-j}$ |
| BEACON alone (No Adjuvant) | | | | | | | 8$^{ij}$ | 0$^j$ |
| CONTROL (No Herbicide) | | | | | | | 0$^j$ | 0$^j$ |

We claim:

1. A silicone glycol-silicone alkane terpolymer having the average formula

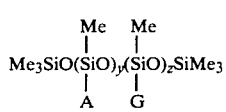

wherein Me denotes a methyl radical, A is a linear or branched alkyl radical having 6 to 24 carbon atoms, G is a glycol moiety having the formula $-R'(OCH_2CH_2$ in which Me denotes a methyl radical, A is a linear or branched alkyl radical having 6 to 24 carbon atoms, m is 12 to 32, y is 0.1 to 1.25 and z is 0.75 to 1.9, with the proviso that when the weight fraction of $-OCH_2CH_2-$ groups is less than 0.7 said alkyl radical A contains from 6 to 12 carbon atoms and when the weight fraction of $-OCH_2CH_2-$ groups is more than 0.8 said alkyl radical A contains from 8 to 24 carbon atoms.

3. The terpolymer according to claim 2, wherein said terpolymer has the average formula 17
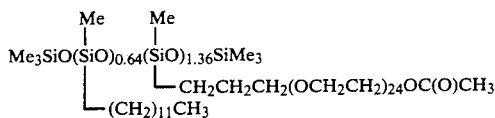
wherein Me denotes a methyl radical.
18
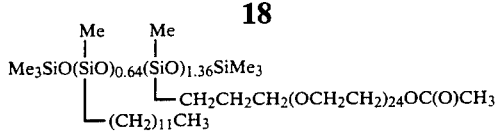
wherein Me denotes a methyl radical.
* * * * *